United States Patent [19]
Hammond

[11] Patent Number: 6,136,529
[45] Date of Patent: *Oct. 24, 2000

[54] **NUCLEIC ACID PROBES TO *MYCOBACTERIUM AVIUM* COMPLEX**

[75] Inventor: Philip W. Hammond, Tehachapi, Calif.

[73] Assignee: Gen-Probe Incorporated, San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/116,984

[22] Filed: Sep. 3, 1993

[51] Int. Cl.$^7$ .............................. C12Q 1/68; C12P 19/34; C07H 21/02; C07H 21/04
[52] U.S. Cl. ........................... 435/6; 435/91.2; 536/24.3; 536/24.31; 536/24.32; 536/24.33
[58] Field of Search .......... 435/6, 91.2; 536/24.3–24.33

[56] References Cited

U.S. PATENT DOCUMENTS

| | | |
|---|---|---|
| 4,851,330 | 7/1989 | Kohne . |
| 5,030,557 | 7/1991 | Hogan et al. . |
| 5,185,439 | 2/1993 | Arnold et al. . |
| 5,422,242 | 6/1995 | Young ........................................ 435/6 |

FOREIGN PATENT DOCUMENTS

| | | |
|---|---|---|
| 0528306 | 2/1993 | European Pat. Off. . |
| 8803957 | 6/1988 | WIPO . |
| 9304201 | 3/1993 | WIPO . |

OTHER PUBLICATIONS

Stahl and Urbance, J. of Bacteriol. 172, 116–124, 1990.
Urbance, J.W., Key, R., and Stahl, D.A., Gen Bank Accession M61684, Jun., 1993.
Wayne and Sramek, "Agents of Newly Recognized or Infrequently Encountered Mycobacterial Diseases," *Clin. Microbiol. Rev.* 5:1–25, (1992).

Frothingham and Wilson, "Sequence–Based Differentiation of Strains in the *Mycobacterium avium* Complex," *J. Bacteriol.* 175:2818–2825 (1993).

Woodley et al., "Evaluation of Syngene DNA–DNA Probe Assays for the Identification of the *Mycobacterum–tuberculosis* Complex and the *Mycobacterium–avium* Complex," *Diagn. Microbiol. Infec. Dis.* 15:657–62 (1992).

Lebrun et al., "Evaluation of Nonradioactive DNA Probes for Identification of Mycobacteria," *J. Clin. Microbiol.* 30:2476–2478 (1992).

Cregan et al., "Use of DNA Probes to Detect *Mycobacterium intracellulare* and "X" Mycobacteria among Clinical Isolates of *Mycobacterium avium* Complex," *J. Infec. Dis.* 166:191–194 (1992).

Viljanen et al., "Conventional Identification Characteristics, Mycolate and Fatty Acid Composition, and Clinical Significance of MAIX AccuProbe–Positive Isolates of *Mycobacterium avium* Complex," *J. Clin. Microbiol.* 31:1376–1378 (1993).

Jonas et al., *Abstract AMS General Meeting* New Orleans, La., (May 1992).

Böddinghaus et al., "Phylogenetic analysis and identification of different serovars of *Mycobacterium intracellulare* at the molecular level," *FEMS Microbiology Letters* 70:197–204, (1990).

Lim et al., "Genotypic Identification of Pathogenic Mycobacterium Species by Using a Nonradioactive Oligonucleotide Probe," *J. Clin. Microbiol.* 29:1276–1278 (1991).

*Primary Examiner*—W. Gary Jones
*Assistant Examiner*—Jeffrey Fredman
*Attorney, Agent, or Firm*—Lyon & Lyon LLP

[57] ABSTRACT

Hybridization assay probes are described which are able to distinguish *Mycobacterium avium* complex organisms from related organisms.

34 Claims, No Drawings

NUCLEIC ACID PROBES TO *MYCOBACTERIUM AVIUM* COMPLEX

FIELD OF THE INVENTION

The invention described and claimed herein relates to the design and use of nucleic acid probes that can detect organisms of the *Mycobacterium avium* complex, in test samples, e.g., from sputum, body fluids, tissue samples, and from cultures.

BACKGROUND OF THE INVENTION

Two single strands of deoxyribo- ("DNA") or ribo- ("RNA") nucleic acid, formed from nucleotides, (including the bases adenine (A), cytosine (C), thymidine (T), guanine (G), uracil (U), or inosine (I)), may hybridize to form a double-stranded structure held together by hydrogen bonds between pairs of complementary bases. Generally, hydrogen bonding occurs between A and T or U, while G or I are hydrogen bonded to C. Along the chain, classical base pairs AT or AU, TA or UA, GC, or CG are present. Additionally, some mismatched base pairs (e.g., AG, GU) may be present.

Bringing together two single strands of nucleic acid containing sufficient contiguous complementary bases, under conditions that promote their hybridization, results in double-stranded nucleic acid. Under appropriate conditions DNA/DNA, RNA/DNA, or RNA/RNA hybrids can form.

A probe is generally a single-stranded oligonucleotide having a nucleotide sequence complementary to some degree to a nucleic acid sequence sought to be detected ("target sequence"). A probe may be labeled with a reporter group such as a radioisotope, a fluorescent or chemiluminescent moiety, or with an enzyme or other ligand that can be used for detection. Kohne, U.S. Pat. No. 4,851,330, and Hogan et al., International Patent Application No. PCT/US87/03009, entitled "Nucleic Acid Probes for Detection and/or Quantitation of Non-Viral Organisms," both references hereby incorporated by reference herein, describe detection of a nucleic acid sequence using nucleic acid hybridization. Hogan et al., supra, also describe methods for determining the presence of a non-viral organism or a group of non-viral organisms in a sample (e.g., sputum, urine, blood, tissue sections, food, soil and water).

Members of the *Mycobacterium avium* complex have characteristic biochemical properties. These members can be differentiated into more than one species by nucleic acid probes and other types of analysis (Wayne and Sramek, *Clin. Microbiol. Rev.* 5:1–25, 1992). The complex includes the species *Mycobacterium avium* and *Mycobacterium intracellulare*. Recent work indicates that the complex also includes additional members. (Wayne and Sramek, supra, Frothingham and Wilson, *J. Bacteriol.* 175:2818 (1993)). Probes which detect members of the *M. avium* complex have been described (Hogan et al., surra; Woodley et al., *Diagn. Microbiol. Infec. Dis.* 15:657–662 (1992); Lebrun et al., *J. Clin. Microbiol.* 30:2476–2478 (1992); Cregan et al., *J. Infec. Dis.* 166:191–194 (1992); Young EPO No. 528 306 A2, application number 92113540.6, "Mycobacterium Primers and Probes," and Liu et al., PCT US92/06821, "Oligonucleotides Complementary to Mycobacterium Nucleic Acids."

SUMMARY OF THE INVENTION

The invention described herein features novel oligonucleotide probes targeted to specific *Mycobacterium avium* complex nucleic acid sequences or having a specified nucleic acid sequence. The probes can hybridize to one or more organisms of the *Mycobacterium avium* complex, other than *Mycobacterium avium* and *Mycobacterium intracellulare*. Preferably the probes also hybridize to *Mycobacterium avium* and *Mycobacterium intracellulare* nucleic acid.

The probes function by hybridizing to target *Mycobacterium avium* complex rRNA or the corresponding DNA gene sequences (rDNA) under stringent hybridization assay conditions. Such hybridization can be detected by techniques known in the art, and as further illustrated herein, to indicate the presence of a *Mycobacterium avium* complex organism.

The probes are particularly useful in an assay to detect and/or quantitate a *Mycobacterium avium* complex organism. The probes distinguish a *Mycobacterium avium* complex organism from other mycobacteria, such as *Mycobacterium tuberculosis, M. kansasii, M. scrofulaceum, M. simiae*, and *M. gordonae*. Viljanen et al., *J. Clin. Microbiol.* 31:1376–1378 (1993), and Jonas et al., *Abstract AMS General Meeting* New Orleans, La., (May 1992), both references hereby incorporated by reference herein, mention the use of a probe corresponding to SEQ ID NO: 1. The probe used in these references was supplied by Gen-Probe Incorporated the assignee of the present application. Neither of these references describe the nucleic acid sequence of the probe. As noted in these references, the probe can detect the presence of the *Mycobacterium avium* complex organisms in species other than *Mycobacterium avium* and *Mycobacterium intracellulare*.

Thus, in a first aspect, the invention described herein features hybridization assay probes preferably 10 to 100, more preferably 22 to 50, nucleotides in length able to hybridize under stringent hybridization assay conditions to a *Mycobacterium avium* complex organism target nucleic acid sequence. Specifically, the hybridization assay probes can hybridize with *Mycobacterium avium* complex targets having the following sequences (written 5' to 3'):

SEQ ID NO: 3: CAUGCGUCUA AAGGUCCUAU CC,
SEQ ID NO: 18: GACAUGCGUC UAAAGGUCC, or
    sequences complementary thereto,
SEQ ID NO: 7: GGAUAGGACC UUUAGACGCA UG and
SEQ ID NO: 16: GGACCUUUAG ACGCAUGUC. As
    would be appreciated by one skilled in the art, probes hybridizing to these sequences can also hybridize to the corresponding DNA sequences.

Complementary sequences can be generated by target amplification techniques such as polymerase chain reaction (PCR) or transcription mediated amplification (e.g., Kacian and Fultz, entitled "Nucleic Acid Amplification Methods," EPO application number 90307503.4; and Kacian et al., U.S. Ser. No. 07/879,685 entitled "Nucleic Acid Sequence Amplification Method, Composition and Kit." Such amplification techniques increase the amount of target sequence and, thus, can be utilized to increase the detection sensitivity of an assay.

"Stringent hybridization assay conditions" refer to conditions wherein the probe hybridizes with target nucleic acid (e.g., rRNA of *Mycobacterium avium* complex organism) and not nucleic acid present in *Mycobacterium tuberculosis, Mycobacterium kansasii, Mycobacterium scrofulaceum, Mycobacterium simiae*, or *Mycobacterium gordonae*. Described below is an example employing stringent hybridization assay conditions comprising hybridization in 0.05 M lithium succinate pH 5.0, 0.6 M LiCl, 1% (w/v) lithium lauryl sulfate, 10 mM ethylenediaminetetraacetic acid (EDTA), 10 mM ethylene glycol bis (beta-amino ethyl ether) N, N, N', N' tetraacetic acid (EGTA) at 60° C. for 15 minutes, followed by the addition of 300 μl of 0.6 M sodium borate pH 8.5, 1% Triton X-100 at 60° C. for 5 minutes. Additional sets of stringent hybridization conditions can be determined based upon techniques known in the art and the present disclosure.

By "probe" is meant to exclude naturally occurring nucleic acids. Purified oligonucleotide probes may be produced by techniques known in the art such as chemical synthesis and in vitro or in vivo expression from recombinant nucleic acid molecules, e.g., retroviral vectors.

An oligonucleotide contains nucleotide subunits covalently joined together. The sugar groups of the nucleotide subunits may be ribose, deoxyribose, or modified derivatives thereof such as O-methyl ribose. The nucleotide subunits may by joined by linkages such as phosphodiester linkages, modified linkages, or may contain non-nucleotide moieties that do not prevent hybridization of the oligonucleotide probe. Modified linkages include those linkages in which a standard phosphodiester linkage is replaced with a different linkage, such as a phosphorothioate linkage or methylphosphonate linkage. When used as a hybridization assay probe, the oligonucleotide preferably contains a reporter group such as an acridinium ester or a radioisotope. Reporter groups help detect hybridization of a probe to its target sequence.

In a related aspect, hybridization assay probes having a specific nucleic acid sequence are described. The probes are complementary to a nucleic acid sequence that varies between a *Mycobacterium avium* complex organism and mycobacteria (e.g., *Mycobacterium tuberculosis, Mycobacterium kansasii, Mycobacterium scrofulaceum, Mycobacterium simiae,* and *Mycobacterium gordonae*). Thus, the probes are useful for detecting and/or quantitating the presence of a *Mycobacterium avium* complex organism.

Specific probes that can hybridize to *Mycobacterium avium* complex nucleic acid and distinguish a *Mycobacterium avium* complex organism from mycobacteria have the following nucleotide sequences (written 5' to 3'):
SEQ ID NO: 1: CATGCGTCTA AAGGTCCTAT CC,
SEQ ID NO: 17: GACATGCGTC TAAAGGTCC, the RNA equivalents thereto
SEQ ID NO: 3: CAUGCGUCUA AAGGUCCUAU CC,
SEQ ID NO: 18: GACAUGCGUC UAAAGGUCC, oligonucleotides complementary thereto
SEQ ID NO: 5: GGATAGGACC TTTAGACGCA TG,
SEQ ID NO: 15: GGACCTTTAG ACGCATGTC, and RNA equivalents to the oligonucleotides complementary thereto
SEQ ID NO: 7: GGAUAGGACC UUUAGACGCA UG, and
SEQ ID NO: 16: GGACCUUUAG ACGCAUGUC. The phrases "have" or "having" mean that the probe consists of the specified nucleotide sequence but may contain additional nucleotides, preferably at its 3' or 5' ends, that do not prevent hybridization under stringent hybridization assay conditions.

Preferably, helper oligonucleotide probes are used with the hybridization assay probes. Hogan and Milliman, U.S. Pat. No. 5,030,557, hereby incorporated by reference herein, describe using helper probes to facilitate the rate of hybridization of a hybridization assay probe to its target nucleic acid. Specific helper probes featured herein consist essentially of the following nucleotide sequences (written 5' to 3'):
SEQ ID NO: 2: GGTATTAGAC CCAGTTTCCC AGGCTATCC CG,
SEQ ID NO: 9: CACCGCAAAA GCTTTCCACC AAAAGA,
SEQ ID NO: 22: TATCCGGTAT TAGACCCAGT TTCCAGGCT TATCCCG,
SEQ ID NO: 25: CCGCGGGCCC ATCCCACACC GCAAAAGCTT TCCACCAAAA, RNA equivalents thereto,
SEQ ID NO: 4: GGUAUUAGAC CCAGUUUCCC AGGCUUAUCC CG,
SEQ ID NO: 10: CACCGCAAAA GCUUUCCACC AAAAGA,
SEQ ID NO: 23: UAUCCGGUAU UAGACCCAGU UUCCAGGCU UAUCCCG
SEQ ID NO: 26: CCGCGGGCCC AUCCCACACC GCAAAAGCUU UCCACCAAAA, oligonucleotides complementary thereto,
SEQ ID NO: 6: CGGGATAAGC CTGGGAAACT GGGTCTAATA CC,
SEQ ID NO: 11: TCTTTTGGTG GAAAGCTTTT GCGGTG,
SEQ ID NO: 19: CGGGATAAGC CTGGGAAACT GGGTCTAATA CCGGATA,
SEQ ID NO: 20: TTTTGGTGGA AAGCTTTTGC GGTGTGGGAT GGGCCCGCGG, and RNA equivalents to the oligonucleotides complementary thereto,
SEQ ID NO: 8: CGGGAUAAGC CUGGGAAACU GGGUCUAAUA CC,
SEQ ID NO: 12: UCUUUUGGUG GAAAGCUUUU GCGGUG,
SEQ ID NO: 21: CGGGAUAAGC CUGGGAAACU GGGUCUAAUA CCGGAUA, and
SEQ ID NO: 24: UUUUGGUGGA AAGCUUUUGC GGUGUGGGAU GGGCCCGCGG.

Helper probes SEQ ID NOs: 2 and 9 are preferably used with assay probe SEQ ID NO: 1. Helper probes SEQ ID NOs: 22 and 25 are preferably used with assay probe SEQ ID NO: 17. When complementary assay probes are used, the corresponding complementary helper probe should also be used. For example, helper probes SEQ ID NOs: 17 and 19 should be used with assay probe SEQ ID NO: 15.

The phrases "consists essentially of" or "consisting essentially of" mean that the probe (helper or hybridization assay probe) is provided as an oligonucleotide that hybridizes under stringent hybridization assay conditions to a nucleic acid sequence of a *Mycobacterium avium* complex organism. The probe may be linked to other nucleic acids that do not prevent hybridization. Helper probes are preferably 10 and 100, most preferably between 15 and 50, nucleotides in length.

In another related aspect, the invention features compositions comprising a nucleic acid hybrid formed between a hybridization assay probe and a nucleic acid sequence substantially complementary thereto (probe:target). "Substantially complementary" means there is sufficient complementarity between the nucleic acids such that the hybrid is stable under stringent hybridization assay conditions. One use of the formed hybrid is to detect the presence of a target sequence. For example, acridinium ester present in hybrids is resistant to hydrolysis in alkaline solution whereas alkaline solution hydrolyses acridinium ester ("AE") present in single-stranded nucleic acid (Arnold et al., entitled "Homogeneous Protection Assay," EPO application number 88308767.8, publication number 309230, hereby incorporated by reference herein). Thus, binding of AE-labeled probe to target can be detected, after hydrolysis of the unbound AE-labeled probe, by measuring chemiluminescence of acridinium ester remaining in the nucleic acid hybrid.

In other related aspects, methods are described for detecting a *Mycobacterium avium* complex organism and distinguishing a *Mycobacterium avium* complex organisms from mycobacteria such as *Mycobacterium tuberculosis, Mycobacterium kansasii, Mycobacterium scrofulaceum, Mycobacterium simiae,* and *Mycobacterium gordonae.* These methods can be used on test samples obtained from human specimens.

The probes of this invention offer a rapid, non-subjective method of identifying and quantitating the presence of specific rRNA sequences unique to the members of the *Mycobacterium avium* complex in a test sample.

Other features and advantages of the invention will be apparent from the following description of the preferred embodiments thereof and from the claims.

DESCRIPTION OF THE PREFERRED EMBODIMENTS

We have identified preferred target sequences present in the rRNA or rDNA of a *Mycobacterium avium* complex organism and designed specific oligonucleotide probes to this sequence. The probes can detect a member of the *Mycobacterium avium* complex, other than *Mycobacterium avium* and *Mycobacterium intracellulare.* Preferably the probes can also detect *Mycobacterium avium* and *Mycobacterium intracellulare.* Also described are helper probes to facilitate hybridization of the assay probe, and methods using the featured probes.

The nucleic acid hybridization assay probes can distinguish a *Mycobacterium avium* complex organism from *M. tuberculosis, M. kansasii, M. scrofulaceum, N. simiae* and *M. gordonae,* under stringent hybridization assay conditions.

Probe sequences were obtained by first obtaining partial or full 16S rRNA sequences of *Mycobacterium avium* complex organisms and mycobacteria. These sequences were then aligned based on regions of sequence homology. Sequence variations were then identified from the aligned sequences and used as target sequences for hybridization assay probes.

Obtaining rRNA Sequences

The featured probes can hybridize to a target nucleic acid sequence from organisms characterized as *Mycobacterium avium* complex which is not *M. avium* or *M. intracellulare.* Preferably, the probes also hybridize to nucleic acid from *M. avium* and *M. intracellulare.* Nucleic acid sequence information for *M. avium* and *M. intracellulare* was obtained as described in Hogan et al., supra, "Nucleic Acid Probes for Detection and/or Quantitation of Non-Viral Organisms," and from published GenBank sequences. Such sequence information is also available from Böddinghaus et al., *FEMS Microbiology Letters* 70:197–204, (1990)).

Nucleic acid sequence information for *Mycobacterium avium* complex organisms not *M. avium* and *M. intracellulare,* was obtained by first identifying such organisms, then characterizing the 16S rRNA. Organisms identified biochemically as *Mycobacterium avium* complex were tested for the *Mycobacterium avium* complex using an AccuProbe test kit (available from Gen-Probe Incorporated). The test kit contains probes which detect the presence of *M. avium* and *M. intracellulare* (AccuProbe *M. avium* Gen-Probe Catalog No. 2835, and AccuProbe *M. intracellulare* Gen-Probe Catalog No. 2840). The 16S rRNA from those organisms that failed to react with species specific *M. avium* and *M. intracellulare* probes was isolated and sequenced using standard techniques known in the art.

These techniques included obtaining nucleic acids using an oligonucleotide primer complementary to a conserved region of 16S rRNA and extending the primer using reverse transcriptase. Nucleic acid sequencing was carried out by the method of dideoxynucleotide chain termination. (e.g., Lane et al., *Proc. Natl. Acad. Sci. USA,* 82: 6955 (1985).)

The nucleic acid sequences from phylogenetically near neighbors, including *M. kansasii, M. scrofulaceum, M. avium, M. intracellulare,* and *M. simiae* were used as comparisons with the nucleic sequence from *Mycobacterium avium* complex organisms to determine variable regions. These sequences were obtained as described by Hogan supra, or from published GenBank sequences.

Probe Design and Hybridization Conditions

To facilitate the identification of a useful probe nucleic acid sequence, the nucleotide sequences from different organisms were first aligned to maximize homology. Within the rRNA molecule there is a close relationship between secondary structure and function. This imposes restrictions on evolutionary changes in the primary sequence so that the secondary structure is maintained. For example, if a base is changed on one side of a helix, a compensating change is made on the other side to preserve the complementarity (this is referred to as co-variance). This allows two very different sequences to be aligned based on the conserved primary sequence and also on the conserved secondary structure elements. Potential target sequences for the hybridization probes were identified by noting variations in the homology of the aligned sequences.

The sequence evolution at each of the variable regions is mostly divergent. Because of the divergence, more distant phylogenetic relatives of *Mycobacterium avium* complex show greater variability to *Mycobacterium avium* complex at the variable region than phylogenetically closer relatives. We observed sufficient variation between *Mycobacterium avium* complex organisms and species of Mycobacterium to identify preferred target sites and design useful probes.

Selective hybridization of probe to target can be accomplished by choosing the appropriate hybridization assay conditions and proper probe design. The stability of the probe:target nucleic acid hybrid should be chosen to be compatible with the assay and washing conditions so that hybrids will only form between highly complementary sequences. Manipulation of one or more of the different assay conditions determines the exact sensitivity and specificity of a particular probe. The following guidelines are useful for designing probes and determining stringent hybridization assay conditions.

Probes should be designed to have an appropriate melting temperature ($T_m$) The appropriate $T_m$ can be obtained by varying the probe length and nucleotide composition (percentage of G+C versus A+T). The probe length and nucleotide composition should preferably be chosen to correspond to a $T_m$ about 2–10° C. higher than the temperature at which the final assay will be performed.

In general, the optimal hybridization temperature for oligonucleotide probes of about 10–50 bases in length is approximately 5° C. below the melting temperature for a given duplex. Incubation at temperatures below the optimum temperature may allow mismatched base sequences to hybridize and can therefore decrease specificity. The longer the probe, the more hydrogen bonding between base pairs and, in general, the higher the $T_m$. Increasing the percentage of G and C also increases the $T_m$ because G–C base pairs exhibit additional hydrogen bonding and therefore greater thermal stability than A–T base pairs.

The preferred method to determine $T_m$ measures hybridization using a Hybridization Protection Assay (HPA) according to Arnold et al., supra entitled "Homogeneous Protection Assay." $T_m$ can be measured using HPA in the following manner. A probe:target hybrid is formed in a lithium succinate buffered solution (0.1 M lithium succinate buffer, pH 5.0, 2 mM EDTA, 2 mM EGTA, 10% (w/v) lithium lauryl sulfate) using an excess amount of target. Aliquots of the hybrid are then diluted in the lithium succinate buffered solution and incubated for five minutes at various temperatures starting below that of the anticipated $T_m$ (typically 55° C.) and increasing in 2–5° C. increments. This solution is then diluted with a mild alkaline borate buffer (0.15 M sodium tetraborate, pH 7.6, 5% (v/v) Triton X-100) and incubated at a lower temperature (for example 50° C.) for ten minutes.

Under these conditions, acridinium ester attached to a single-stranded probe is hydrolyzed while acridinium ester attached to hybridized probe is relatively protected from hydrolysis. Thus, the amount of acridinium ester remaining is proportional to the amount of hybrid and can be measured by the chemiluminescence produced from the acridinium ester upon the addition of hydrogen peroxide followed by alkali. Chemiluminescence can be measured in a luminometer (e.g., the Gen-Probe LEADER I or LEADER 50 luminometers). The resulting data is plotted as percent of maximum signal (usually from the lowest temperature) versus temperature. The $T_m$ is defined as the temperature at which 50% of the maximum signal remains. In addition to the method above, $T_m$ may be determined by isotopic methods well known to those skilled in the art (e.g., Hogan et al., supra).

The $T_m$ for a given hybrid varies depending on the hybridization solution used. Factors such as the salt concentration, detergents, and other solutes can affect hybrid stability during thermal denaturation (J. Sambrook, E. F. Fritsch and T. Maniatis, *Molecular Cloning*, ch. 11 (2d ed. 1989)). Thus, thermal stability of hybrids increases as the ionic strength of the reaction mixture increases. On the other hand, chemical reagents which disrupt hydrogen bonds, such as formamide, urea, dimethyl sulfoxide and alcohols, can greatly reduce the thermal stability of a hybrid.

To ensure specificity of a probe to its target, it is desirable to have probes which hybridize only under conditions of high stringency. Under conditions of high stringency only highly complementary nucleic acid hybrids will form; hybrids without a sufficient degree of complementarity will not form. Accordingly, the stringency of the assay conditions determines the amount of complementarity needed between two nucleic acid strands to form a hybrid. Stringency is chosen to maximize the difference in stability between the hybrid formed with the target and other nucleic acid sequences.

Proper specificity may be achieved by minimizing the length of perfect complementarity to non-target organisms, avoiding G and C rich regions of homology to non-target sequences, and by constructing the probe to contain as many destabilizing mismatches to non-target sequences as possible. Whether a probe sequence is useful to detect only a specific type of organism depends largely on the thermal stability difference between probe:target hybrids versus probe:non-target hybrids. In designing probes, the differences in these $T_m$ values should be as large as possible (preferably 2° C.–5° C. or more).

The length of the target nucleic acid sequence, and accordingly the length of the probe sequence, can also be important. In some cases, there may be several sequences from a particular region, varying in location and length, which yield probes with the desired hybridization characteristics. In other cases, one sequence may be significantly better than another which differs merely by a single base.

While it is possible for nucleic acids that are not perfectly complementary to hybridize, the longest stretch of complementarity generally determines hybrid stability. Oligonucleotide probes of different lengths and base composition may be used. Preferably, oligonucleotide assay probes are between 10 to 100 and, more preferably, between 22 to 50 bases in length.

Regions of rRNA known to form strong internal structures inhibitory to hybridization are less preferred target regions. Likewise, probes with extensive self-complementarity should be avoided. As explained above, hybridization is the association of two single strands of complementary nucleic acid to form a hydrogen-bonded double strand. It is implicit that if one of the two strands is wholly or partially involved in an intramolecular or intermolecular hybrid it will be less able to participate in the formation of a new intermolecular probe:target hybrid. The rRNA molecule is known to form very stable intramolecular hybrids. By designing a probe so that a substantial portion of the targeted sequence is single-stranded, the rate and extent of hybridization between probe and target may be greatly increased.

An rDNA target occurs naturally in a double-stranded form as does the product of the polymerase chain reaction (PCR). These double-stranded targets are naturally inhibitory to hybridization with a probe and require denaturation prior to hybridization. Appropriate denaturation and hybridization conditions are known in the art (e.g., E. M. Southern, *J. Mol. Biol.* 98:503 (1975)).

Probe Synthesis

Once a presumptive unique target sequence has been identified, a complementary oligonucleotide probe is selected and synthesized. Defined oligonucleotide probes may be produced by any of several well-known methods, including automated solid-phase chemical synthesis using cyanoethylphosphoramidite precursors (Barone et al., *Nucleic Acids Research* 12:4051 (1984)), and as described in J. Sambrook, E. F. Fritsch and T. Maniatis, *Molecular Cloning*, ch. 11 (2d ed. 1989). Following synthesis and purification of a particular oligonucleotide probe, several different procedures may be utilized to determine the acceptability of the probe in terms of size and purity. One such procedure is polyacrylamide gel electrophoresis. Another such procedure is High Pressure Liquid Chromatography ("HPLC"). These procedures are well known to those skilled in the art.

Oligonucleotide probes may be labeled with a reporter group by any of several well-known methods (e.g., supra, J. Sambrook et al.). Useful labels include radioisotopes and non-radioactive reporting groups. Isotopic labels include $^3$H, $^{35}$S, $^{32}$P, $^{125}$I, $^{57}$Co and $^{14}$C. Isotopic labels can be introduced into the oligonucleotide by techniques known in the art such as nick translation, end labeling, second strand synthesis, the use of reverse transcription, and by chemical methods. When using radiolabeled probes hybridization can be detected by autoradiography, scintillation counting, or gamma counting. The detection method selected will depend upon the particular radioisotope label.

Non-isotopic materials can also be used for labeling, and may be introduced internally into the nucleic acid sequence or at the end of the nucleic acid sequence. Modified nucleotides may be incorporated enzymatically or chemically. Chemical modifications of the probe may be performed during or after synthesis of the probe, for example, through the use of non-nucleotide linker groups as described by Arnold et al., entitled "Non-Nucleotide Linking Reagents for Nucleotide Probes," EPO application number 88308766.0, publication number 313219, hereby incorporated by reference herein. Non-isotopic labels include fluorescent molecules, chemiluminescent molecules, enzymes, cofactors, enzyme substrates, haptens or other ligands.

Preferably, the probes are labeled with an acridinium ester. Acridinium ester labeling may be performed as described by Arnold et al., U.S. Pat. No. 5,185,439, hereby incorporated by reference herein.

Helper Probes

The rate of nucleic acid hybridization of an assay probe with its target nucleic acid is enhanced by using Helper Probes as described in Hogan and Milliman, supra. Helper probes are selected to hybridize to nucleic acid sequences located near the region targeted by the assay probe. Hybridization of the helper probe alters the secondary and tertiary structure and thereby renders the targeted area of the nucleic acid more accessible for the assay probe. Helper probes to be used with the assay probes described herein include oligonucleotides having the following nucleotide sequences of SEQ ID NOs: 2, 9, 22, and 25; the RNA equivalents thereto, SEQ ID NOs: 4, 10, 23 and 26; oligonucleotides complementary thereto, SEQ ID NOs: 6, 11, 19 and 20; and RNA equivalents to the oligonucleotides complementary thereto, SEQ ID Nos: 8, 12, 21, and 24.

EXAMPLES

Examples are provided below to illustrate different aspects and embodiments of the present invention. These examples are not intended in any way to limit the disclosed invention.

The probes were synthesized with a non-nucleotide linker as described by Arnold et al. supra, "Non-Nucleotide Linking Reagents For Nucleotide Probes," then labeled with a chemiluminescent acridinium ester as described by Arnold et al., supra, U.S. Pat. No. 5,185,439. The reactivity and specificity of the probes for *Mycobacterium avium* complex organisms were demonstrated using an HPA format. These procedures are described by Arnold et al., supra, "Homogeneous Protection Assay"; and Arnold et al., *Clin. Chem.*, 35:1588 (1989) (hereby incorporated by reference herein).

Results are given in relative light units (RLU). Probes were hybridized to a cell lysate or RNA purified according to J. Sambrook, E. F. Fritsch and T. Maniatis, *Molecular Cloning* (2d ed. 1989). Alternatively, lysates, especially of mycobacteria, Gram positive organisms, or yeasts, could be obtained utilizing a method described by Murphy et al., "Method for Releasing RNA and DNA from Cells," EPO application number 87303641.2, publication number 288618, hereby incorporated by reference herein. The following examples describe hybridization assay probes targeted to *Mycobacterium avium* complex rRNA sequences, or the corresponding gene, and their use in a hybridization assay.

Example 1

This example illustrates the ability of an acridinium ester-labeled probe targeted to *Mycobacterium avium* complex 16S rRNA to detect *Mycobacterium avium* complex organisms but not other microorganisms. The mixture contained an acridinium ester-labeled assay probe having SEQ ID NO: 1, and unlabeled Helper Probes, SEQ ID NOs: 2 and 9.

Table 1 presents data using these probes with an excess of RNA released from solid medium containing $10^6$–$10^9$ organisms. Nucleic acids from 0.1 ml of cell lysate were hybridized with the probe mixture in a hybridization solution containing 0.05 M lithium succinate pH 5, 0.6 M LiCl, 1% (w/v) lithium lauryl sulfate, 10 mM EDTA, 10 mM EGTA at 60° C. for 15 minutes, followed by addition of 300 µl of 0.6 M sodium borate pH 8.5, 1% Triton X-100 at 60° C. for 5 minutes. The addition of the alkaline solution hydrolyses the acridinium present on single stranded probe. The chemiluminescence from the hybridized acridinium ester-labeled probes was measured in a luminometer equipped with automatic injection of 0.1% hydrogen peroxide in 1 mM nitric acid, followed by injection of a 1 N sodium hydroxide solution. The data in Table 1 show that the probe hybridizes to organisms from clinical isolates classified, by gas liquid chromatography (GLC) or biochemically, as members of the *Mycobacterium avium* complex including the species *Mycobacterium avium* and *Mycobacterium intracellulare*.

TABLE 1

| CLINICAL ISOLATE | CLINICAL CLASSIFICATION | RLU |
|---|---|---|
| 558 | M. chelonae | 1327 |
| 550 | M. chelonae | 1726 |
| 547 | M. avium | 19753 |
| 546 | M. asiaticum | 1591 |
| 538 | M. asiaticum | 1640 |
| 534 | M. asiaticum | 1571 |
| 516 | M. asiaticum | 1102 |
| 431 | M. asiaticum | 718 |
| 304 | M. intracellulare | 362682 |
| 301 | M. intracellulare | 318099 |
| 317 | M. intracellulare | 305916 |
| 272 | M. intracellulare | 300990 |
| 315 | M. intracellulare | 266369 |
| 94 | M. avium | 67548 |
| 141 | M. avium | 64377 |
| 256 | M. avium | 64249 |
| 103 | M. avium | 57124 |
| 129 | M. avium | 53531 |
| 242 | M. avium | 47153 |
| 238 | M. avium | 45754 |
| 166 | M. avium | 40656 |
| 118 | M. avium | 31662 |
| L48956 | MAC | 428019 |
| L46117 | MAC | 393962 |
| 35 | MAC | 393070 |
| L7536 | MAC | 381641 |
| L65266 | MAC | 360451 |
| L22287 | MAC | 354270 |
| L35124 | MAC | 353739 |
| L48624 | MAC | 341437 |
| M26426 | MAC | 333808 |
| L35750 | MAC | 333282 |
| T2427 | MAC | 331029 |
| L7630 | MAC | 328488 |
| L54133 | MAC | 320079 |
| L65219 | MAC | 312054 |
| L44447 | MAC | 296561 |
| L69310 | MAC | 293500 |
| L46711 | MAC | 277768 |
| H42971 | MAC | 270324 |
| W3158 | MAC | 263145 |
| H49080 | MAC | 207270 |
| L140 | MAC | 203348 |
| L48031 | MAC | 182882 |
| L48806 | MAC | 173667 |
| L63176 | MAC | 156333 |
| L47860 | MAC | 139657 |
| W26279 | MAC | 111730 |
| L52658 | MAC | 92395 |
| L61554 | MAC | 74266 |
| L67286 | MAC | 55908 |
| H42888 | MAC | 47523 |
| L63069 | MAC | 46477 |
| W21264 | MAC | 45655 |
| L47338 | MAC | 44941 |
| CAPE09 | MAC | 40584 |
| L2804 | MAC | 38436 |
| L62938 | MAC | 33957 |

TABLE 1-continued

| CLINICAL ISOLATE | CLINICAL CLASSIFICATION | RLU |
|---|---|---|
| L492 | MAC | 32644 |
| L52852 | MAC | 26818 |
| L25342 | MAC | 26214 |
| L34366 | MAC | 11964 |
| 391 | MAC | 6640 |
| 392 | MAC | 4512 |
| 393 | MAC | 4371 |
| 365 | MAC | 2841 |

MAC refers to organisms belonging to the *Mycobacterium avium* complex. In some cases these isolates are neither *M. avium* nor *M. intracellulare*, but are classified in the complex based on biochemical data or GLC analysis. Organisms were characterized as *Mycobacterium avium* complex (MAC) positive by GLC (Stockman et al., Abstract 1059, "Current Status of a Rapid Method to Identify Mycobacteria Using Cell Wall Fatty Acid Analysis," 28$^{th}$ International ICACC, Los Angeles Calif. (1988)) or biochemically (e.g., Mayo Clinic Procedure Manual (1988); or Kent and Kubica, *Public Health Mycobacteriology A Guide For The Level III Laboratory*, U.S. Department of Health and Human Services (1985)).

Table 2 also shows the ability of the probe mix containing acridinium ester-labeled assay probe having SEQ ID NO: 1, and unlabeled Helper Probes, SEQ ID NOs: 2 and 9, to distinguish *Mycobacterium avium* complex organisms from other species of mycobacteria. The same experimental conditions were used as in Table 1.

An all-bacteria/yeast probe mixture was used as a control to demonstrate the presence of bacterial nucleic acid. Hogan et al., supra, entitled "Nucleic Acid Probes for Detection and/or Quantitation of Non-Viral Organisms," gives examples of suitable all-bacteria/yeast probe mixtures. The all-bacteria probe used in the examples described herein is a derivative of all-bacteria probe No. 7 described by Hogan et al., (the all-bacteria probe used in the examples described herein is shifted so that it is four nucleotides shorter on the 5' end but 5 bases longer on the 3' end probe than the Hogan probe No. 7). The yeast probe is a derivative of fungal probe No. 1 described in Hogan et al.

TABLE 2

| Organism | ATCC NO. | Bacterial Probe RLU | SEQ ID NO. 1 RLU |
|---|---|---|---|
| Mycobacterium acapulcensis | 14473 | 678,594 | 615 |
| Mycobacterium africanum | 25420 | 1,365,677 | 1,024 |
| Mycobacterium agri | 27406 | 505,650 | 934 |
| Mycobacterium aichiense | 27280 | 825,527 | 861 |
| Mycobacterium asiaticum | 25276 | 561,851 | 684 |
| Mycobacterium aurum | 23366 | 179,023 | 663 |
| Mycobacterium avium | 25291 | 856,936 | 130,205 |
| Mycobacterium austroafricanum | 33464 | 175,943 | 678 |
| Mycobacterium bovis | 19210 | 81,001 | 692 |
| Mycobacterium bovis BCG | 35734 | 1,238,645 | 545 |
| Mycobacterium chelonae | 14472 | 704,763 | 889 |
| Mycobacterium chelonae ssp. abscessus | 19977 | 540,599 | 880 |
| Mycobacterium chelonae ssp. chelonae | 35752 | 203,455 | 998 |
| Mycobacterium chelonae chemovar niacinogenes | 35750 | 369,397 | 795 |
| Mycobacterium chitae | 19627 | 660,560 | 589 |
| Mycobacterium chubuense | 27278 | 546,614 | 627 |
| Mycobacterium dierhoferi | 19340 | 92,730 | 619 |
| Mycobacterium duvalii | 43910 | 22,855 | 534 |

TABLE 2-continued

| Organism | ATCC NO. | Bacterial Probe RLU | SEQ ID NO. 1 RLU |
|---|---|---|---|
| Mycobacterium engbaekii | 27353 | 316,360 | 537 |
| Mycobacterium farcinogenes | 35753 | 310,917 | 615 |
| Mycobacterium flavescens | 14474 | 109,310 | 619 |
| Mycobacterium fortuitum | 6841 | 90,272 | 671 |
| Mycobacterium fortuitum ssp. acetamidolyticum | 35931 | 187,320 | 492 |
| Mycobacterium gadium | 27726 | 67,936 | 605 |
| Mycobacterium gallinarum | 19710 | 229,683 | 585 |
| Mycobacterium gastri | 15754 | 561,845 | 779 |
| Mycobacterium gilvum | 43909 | 466,478 | 482 |
| Mycobacterium gordonae | 14470 | 416176 | 718 |
| Mycobacterium haemophilum | 29548 | 1,305,824 | 2,413 |
| Mycobacterium intracellulare | 13950 | 371,430 | 516,219 |
| Mycobacterium kansasii | 12478 | 385819 | 959 |
| Mycobacterium komossense | 33013 | 46,384 | 730 |
| Mycobacterium lactis | 27356 | 271,283 | 624 |
| Mycobacterium malmoense | 29571 | 255,434 | 945 |
| Mycobacterium marinum | 927 | 60,723 | 568 |
| Mycobacterium moriokaense | 43059 | 29,899 | 7,408 |
| Mycobacterium nonchromogenicum | 19530 | 363,510 | 1,182 |
| Mycobacterium novum | 19619 | 123,882 | 1,160 |
| Mycobacterium obuense | 27023 | 41,480 | 578 |
| Mycobacterium parafortuitum | 19686 | 273,792 | 614 |
| Mycobacterium petroleophilum | 21497 | 613,185 | 764 |
| Mycobacterium phlei | 11758 | 268,973 | 447 |
| Mycobacterium porcinum | 33776 | 93,781 | 761 |
| Mycobacterium poriferae | 35087 | 124,751 | 573 |
| Mycobacterium pulveris | 35154 | 200,416 | 814 |
| Mycobacterium rhodesiae | 27024 | 676,893 | 858 |
| Mycobacterium scrofulaceum | 19981 | 91,691 | 625 |
| Mycobacterium shimoidei | 27962 | 1,345,704 | 566 |
| Mycobacterium simiae | 25275 | 163,534 | 716 |
| Mycobacterium smegmatis | 14468 | 40,771 | 866 |
| Mycobacterium spagni | 33027 | 132,994 | 800 |
| Mycobacterium szulgai | 35799 | 194,004 | 731 |
| Mycobacterium terrae | 15755 | 117,411 | 816 |
| Mycobacterium thermoresitibile | 19527 | 51,481 | 572 |
| Mycobacterium tokaiense | 27282 | 32,065 | 525 |
| Mycobacterium triviale | 23292 | 1,285,307 | 4,535 |
| Mycobacterium tuberculosis | 25177 | 458,155 | 781 |
| Mycobacterium tuberculosis | 27294 | 79,745 | 796 |
| Mycobacterium ulcerans | 19423 | 535,428 | 628 |
| Mycobacterium vaccae | 15483 | 921,869 | 826 |
| Mycobacterium valentiae | 29356 | 67,470 | 461 |
| Mycobacterium xenopi | 19250 | 148,489 | 586 |

Table 3 shows that the assay probe mixture described above distinguishes *Mycobacterium avium* complex from members of a phylogenetic cross section panel of microbes. The all-bacteria/yeast probe mixture was also used as a control in this experiment.

TABLE 3

| ORGANISM | ATCC # | ALL BACT PROBE RLU | SEQ ID NO 1 RLU |
|---|---|---|---|
| Acinetobacter calcoaceticus | 33604 | 1437305 | 2162 |
| Actinomadura madurae | 19425 | 659806 | 5788 |
| Actinomyces pyogenes | 19411 | 1665711 | 1375 |
| Actinoplanes italicus | 27366 | 879698 | 1790 |
| Arthrobacter oxydans | 14358 | 1523527 | 6567 |
| Bacillus subtilis | 6051 | 1345729 | 2153 |
| Bacteriodes fragilis | 23745 | 1750909 | 1825 |
| Bordetella bronchiseptica | 10580 | 1726027 | 1097 |
| Branhamella catarrhalis | 25238 | 1328969 | 957 |
| Brevibacterium linens | 9172 | 274844 | 10841 |
| Campylobacter jejuni | 33560 | 1558313 | 699 |
| Candida albicans | 18804 | 5406 | 768 |
| Chromobacterium violaceum | 29094 | 1403217 | 1101 |
| Clostridium innocuum | 14501 | 993375 | 741 |

TABLE 3-continued

| ORGANISM | ATCC # | ALL BACT PROBE RLU | SEQ ID NO 1 RLU |
|---|---|---|---|
| *Clostridium perfringens* | 13124 | 1731773 | 825 |
| *Corynebacterium aquaticum* | 14665 | 1398949 | 10593 |
| *Corynebacterium diphtheriae* | 11913 | 872919 | 14093 |
| *Corynebacterium genitalium* | 33030 | 1228750 | 1465 |
| *Corynebacterium haemolyticum* | 9345 | 1947465 | 724 |
| *Corynebacterium matruchotii* | 33806 | 1497644 | 17984 |
| *Corynebacterium minutissimum* | 23347 | 215637 | 13926 |
| *Corynebacterium pseudodiphtheriticum* | 10700 | 1135347 | 9780 |
| *Corynebacterium pseudogenitalium* | 33035 | 704512 | 1831 |
| *Corynebacterium pseudotuberculosis* | 19410 | 1511610 | 12569 |
| *Corynebacterium renale* | 19412 | 1438708 | 6146 |
| *Corynebacterium striatum* | 6940 | 1544873 | 8463 |
| *Corynebacterium xerosis* | 373 | 257020 | 8938 |
| *Deinococcus radiodurans* | 35073 | 1830432 | 1126 |
| *Dermatophilus congolensis* | 14637 | 177084 | 4985 |
| *Erysipelothrix rhusiopathiae* | 19414 | 355905 | 540 |
| *Escherichia coli* | 10798 | 1630489 | 1441 |
| *Flavobacterium meniningosepticum* | 13253 | 941501 | 780 |
| *Haemophilus influenzae* | 19418 | 1674122 | 1069 |
| *Klebsiella pneumoniae* | 23357 | 1037335 | 911 |
| *Lactobacillus acidophilus* | 4356 | 126342 | 672 |
| *Legionella pneumophila* | 33152 | 1002154 | 3469 |
| *Microbacterium lacticum* | 8180 | 1464125 | 464 |
| *Neisseria meningtidis* | 13077 | 1878115 | 1295 |
| *Nocardia asteriodes* | 19247 | 1096320 | 5680 |
| *Nocardia brasiliensis* | 19296 | 1496142 | 6867 |
| *Nocardia otitidis-caviarum* | 14629 | 500853 | 2103 |
| *Nocardiopsis dassonvillei* | 23218 | 650930 | 2501 |
| *Oerskovia turbata* | 33225 | 402465 | 532 |
| *Oerskovia xanthineolytica* | 27402 | 1143957 | 1852 |
| *Paracoccus denitrificans* | 17741 | 750688 | 811 |
| *Propionibacterium acnes* | 6919 | 1561987 | 503 |
| *Proteus mirabilis* | 25933 | 1678893 | 2112 |
| *Pseudomonas aeruginosa* | 25330 | 909012 | 2086 |
| *Rahnella aquatilis* | 33071 | 1855309 | 1147 |
| *Rhodococcus aichiensis* | 33611 | 1256464 | 5702 |
| *Rhodococcus aurantiacus* | 25936 | 1422552 | 6870 |
| *Rhodococcus bronchialis* | 25592 | 1107984 | 4915 |
| *Rhodococcus chubuensis* | 33609 | 521704 | 3248 |
| *Rhodococcus equi* | 6939 | 800836 | 1575 |
| *Rhodococcus obuensis* | 33610 | 2712961 | 4856 |
| *Rhodococcus sputi* | 29627 | 601759 | 5279 |
| *Rhodospirillum rubrum* | 11170 | 1145318 | 621 |
| *Staphylococcus aureus* | 12598 | 1409535 | 906 |
| *Staphylococcus epidermidis* | 12228 | 1685887 | 668 |
| *Streptococcus mitis* | 9811 | 1804371 | 542 |
| *Streptococcus pneumoniae* | 6306 | 1856485 | 418 |
| *Streptococcus pyogenes* | 19615 | 1710308 | 721 |
| *Streptomyces griseus* | 23345 | 1528989 | 8647 |
| *Vibrio parahaemolyticus* | 17802 | 1594489 | 1142 |
| *Yersinia enterocolitica* | 9610 | 1269995 | 3565 |
| *Mycobacterium avium complex* | | 113698 | 244159 |

Example 2

This example illustrates the use of an assay probe of the same sense as the *Mycobacterium avium* complex target nucleic acid to detect the products of nucleic acid amplification. rRNA from a clinical isolate of an organism biochemically classified as *Mycobacterium avium* complex (MAC) but not reactive with AccuProbe *M. avium* or *M. intracellulare* species-specific probes, was amplified by incubating at 42° C. for two hours in 100 μL of a solution containing 0.15 μM of a promoter-primer (SEQ ID NO: 13), 0.15 μM of a primer (SEQ ID NO: 14), 75 mM Tris-HCl pH 8.5, 35 mM KCl, 20 mM MgCl$_2$, 15 mM N-acetyl cysteine, 4 mM rATP, 4 mM rCTP, 4 mM rGTP, 4 mM rUTP, 0.2 mM DATP, 0.2 mM dCTP, 0.2 mM dGTP, 0.2 mM dTTP, 5% glycerol, 900 U MuMLV reverse transcriptase and 400 U T7 RNA polymerase (See, Kacian et al., supra, entitled "Nucleic Acid Sequence Amplification Method, Composition, and Kit.") The reaction was heated to 95° C. for 5 minutes prior to addition of the enzymes.

The assay probe having the nucleic acid sequence of SEQ ID NO: 15, which contains the same sense as the target rRNA, was used in conjunction with helper probes SEQ ID NOs: 19 and 20 to detect the presence of a *Mycobacterium avium* complex organism from amplified nucleic acid. Detection was carried out as described in Example 1. As shown in Table 4, the probe (SEQ ID NO: 15) detected the presence of this *Mycobacterium avium* complex isolate, which could not be detected with species-specific probes AccuProbe *M. avium* or AccuProbe *M. intracellulare*.

TABLE 4

| Target | RLU |
|---|---|
| 50 fg MAC isolate rRNA | 91,713 |
| 250 fg MAC isolate rRNA | 384,252 |
| 0 target | 3,274 |

The data shown in the various examples described above confirm that the novel probes herein described and claimed are capable of distinguishing a *Mycobacterium avium* complex organism from mycobacteria. Furthermore, complementary oligonucleotide probes, i.e., those having the same sense as the target, are useful to detect the products of a target amplification procedures.

Other embodiments are within the following claims.

I claim:

1. A nucleic acid hybridization assay probe 22 to 100 bases in length for detecting a *Mycobacterium avium* complex organism, said probe comprising a nucleic acid sequence selected from the group consisting of:
SEQ ID NO: 1: CATGCGTCTA AAGGTCCTAT CC,
SEQ ID NO: 3: CAUGCGUCUA AAGGUCCUAU CC,
SEQ ID NO: 5: GGATAGGACC TTTAGACGCA TG, and
SEQ ID NO: 7: GGAUAGGACC UUUAGACGCA UG.

2. A probe mix comprising:
a) a nucleic acid hybridization assay probe 22 to 100 bases in length for detecting a *Mycobacterium avium* complex organism under hybridization assay conditions said probe having a subsequence which consists of a detection sequence selected from the group consisting of:
SEQ ID NO: 1: CATGCGTCTA AAGGTCCTAT CC,
SEQ ID NO: 3: CAUGCGUCUA AAGGUCCUAU CC,
SEQ ID NO: 5: GGATAGGACC TTTAGACGCA TG, and
SEQ ID NO: 7: GGAUAGGACC UUUAGACGCA UG;
wherein under said hybridization conditions said hybridization assay probe will hybridize to nucleic acid from said *Mycobacterium avium* complex organism to form a detectable probe:target hybrid and said hybridization assay probe will not hybridize under said hybridization conditions with nucleic acid from *Mycobacterium tuberculosis, Mycobacterium kansasii, Mycobacterium scrofulaceum, Mycobacterium simiae*, and *Mycobacterium gordonae* to form a detectable probe:non-target hybrid; and
b) a helper probe consisting of a helper sequence selected from the group consisting of:
SEQ ID NO: 2: GGTATTAGAC CCAGTTTCCC AGGCTTATCC CG,
SEQ ID NO: 4: GGUAUUAGAC CCAGUUUCCC AGGCWUAUCC CG,
SEQ ID NO: 6: CGGGATAAGC CTGGGAAACT GGGTCTAATA CC,
SEQ ID NO: 8: CGGGAUAAGC CUGGGAAACU GGGUCUAAUA CC,
SEQ ID NO: 9: CACCGCAAAA GCTTTCCACC AAAAGA,
SEQ ID NO: 10: CACCGCAAAA GCUUUCCACC AAAAGA,
SEQ ID NO: 11: TCTTTTGGTG GAAAGCTTTT GCGGTG, and
SEQ ID NO: 12: UCUUUUGGUG GAAAGCUUUU GCGGUG.

3. The probe mix of claim 2, wherein said hybridization assay probe consists of said detection sequence and at least one detectable label.

4. A composition for detecting a *Mycobacterium avium* complex organism comprising a nucleic acid hybrid, which is stable under high stringency hybridization assay conditions, formed between an oligonucleotide 22 to 50 bases in length having a subsequence which consists of a nucleic acid sequence selected from the group consisting of:
SEQ ID NO: 1: CATGCGTCTA AAGGTCCTAT CC,
SEQ ID NO: 3: CAUGCGUCUA AAGGUCCUAU CC,
SEQ ID NO: 5: GGATAGGACC TTTAGACGCA TG, and
SEQ ID NO: 7: GGAUAGGACC UUUAGACGCA UG,
and a nucleotide polymer substantially complementary thereto, wherein under said hybridization conditions said oligonucleotide will hybridize to nucleic acid from said *Mycobacterium avium* complex organism to form a detectable oligonucleotide:target hybrid and said oligonucleotide will not hybridize under said conditions with nucleic acid from *Mycobacterium tuberculosis, Mycobacterium kansasii, Mycobacterium scrofulaceum, Mycobacterium simiae*, and *Mycobacterium gordonae* to form a detectable oligonucleotide:non-target hybrid.

5. A method for detecting the presence of a *Mycobacterium avium* complex organism in a sample suspected of containing *Mycobacterium intracellulare*, and suspected of containing *Mycobacterium avium*, and distinguishing the presence of said *Mycobacterium avium* complex organism from *Mycobacterium tuberculosis, Mycobacterium kansasii, Mycobacterium scrofulaceum, Mycobacterium simiae*, and *Mycobacterium gordonae*, comprising the steps of:
a) contacting said sample suspected of containing *Mycobacterium intracellulare* and suspected of containing *Mycobacterium avium* under hybridization assay conditions with a nucleic acid hybridization assay probe able to hybridize under said hybridization assay conditions to a target nucleic acid sequence present in *Mycobacterium avium* and *Mycobacterium intracellulare* nucleic acid, said hybridization assay probe comprising a nucleic acid sequence selected from the group consisting of:

SEQ ID NO: 1: CATGCGTCTA AAGGTCCTAT CC,
SEQ ID NO: 3: CAUGCGUCUA AAGGUCCUAU CC,
SEQ ID NO: 5: GGATAGGACC TTTAGACGCA TG, and
SEQ ID NO: 7: GGAUAGGACC UUUAGACGCA UG, wherein under said hybridization conditions said hybridization assay probe will hybridize to nucleic acid from *Mycobacterium avium* and *Mycobacterium intracellulare* to form a detectable probe:target hybrid and said hybridization assay probe will not hybridize under said hybridization conditions with nucleic acid from *Mycobacterium tuberculosis, Mycobacterium kansasii, Mycobacterium scrofulaceum, Mycobacterium simiae*, and *Mycobacterium gordonae* to form a detectable probe:non-target hybrid; and b) detecting the presence of said detectable probe:target as an indication of the presence of *Mycobacterium intracellulare* or *Mycobacterium avium* in said sample.

6. A method for detecting the presence of a *Mycobacterium avium* complex organism in a sample suspected of containing *Mycobacterium intracellulare*, suspected of containing *Mycobacterium avium*, and suspected of containing a *Mycobacterium avium* complex organism other than *Mycobacterium intracellulare* and *Mycobacterium avium* comprising the steps of (a) contacting said sample suspected of containing *Mycobacterium avium*, suspected of containing *Mycobacterium intracellulare*, and suspected of containing said *Mycobacterium avium* complex organism other than *Mycobacterium intracellulare* and *Mycobacterium avium* under hybridization assay conditions with an oligonucleotide probe comprising a nucleotide base sequence consisting of a sequence selected from the group consisting of:

SEQ ID NO: 1: CATGCGTCTA AAGGTCCTAT CC,
SEQ ID NO: 3: CAUGCGUCUA AAGGUCCUAU CC,
SEQ ID NO: 5: GGATAGGACC TTTAGACGCA TG, and
SEQ ID NO: 7: GGAUAGGACC UUUAGACGCA UG, wherein under said hybridization conditions said hybridization assay probe will hybridize to nucleic acid from *Mycobacterium avium, Mycobacterium intracellulare,* and said *Mycobacterium avium* complex organism other than *Mycobacterium avium* and *Mycobacterium intracellulare* to form a detectable probe:target hybrid and said hybridization assay probe will not hybridize under said hybridization conditions with nucleic acid from *Mycobacterium tuberculosis, Mycobacterium kansasii, Mycobacterium scrofulaceum, Mycobacterium simiae*, and *Mycobacterium gordonae* to form a detectable probe:non-target hybrid and (b) detecting the formation of said probe:target hybrid as an indication that *Mycobacterium avium, Mycobacterium intracellulare,* or said *Mycobacterium avium* complex organism other than *Mycobacterium avium* or *Mycobacterium intracellulare* may be present is said sample.

7. The method of claim 6 further comprising the presence of a helper probe in said step (a), said helper probe having a helper sequence selected from the group consisting of:

SEQ ID NO: 2: GGTATTAGAC CCAGTTTCCC AGGCTTATCC CG,
SEQ ID NO: 4: GGUAUUAGAC CCAGUUUCCC AGGCWUAUCC CG,
SEQ ID NO: 6: CGGGATAAGC CTGGGAAACT GGGTCTAATA CC,
SEQ ID NO: 8: CGGGAUAAGC CUGGGAAACU GGGUCUAAUA CC,
SEQ ID NO: 9: CACCGCAAAA GCTTTCCACC AAAAGA,
SEQ ID NO: 10: CACCGCAAAA GCUUUCCACC AAAAGA,
SEQ ID NO: 11: TCTTTTGGTG GAAAGCTTTT GCGGTG, and
SEQ ID NO: 12: UCUUUUGGUG GAAAGCUUUU GCGGUG, wherein said helper probe is up to 50 bases in length.

8. The method of claim 7, wherein said helper probe consists of said helper sequence.

9. A nucleic acid hybridization assay probe 19 to 100 bases in length for detecting a *Mycobacterium avium* complex organism, said probe comprising a nucleic acid sequence selected from the group consisting of:

SEQ ID NO: 15: GGACCTTTAG ACGCATGTC,
SEQ ID NO: 16: GGACCUUUAG ACGCAUGUC,
SEQ ID NO: 17: GACATGCGTC TAAAGGTCC, and
SEQ ID NO: 18: GACAUGCGUC UAAAGGUCC.

10. A probe mix comprising a) a nucleic acid hybridization assay probe 19 to 100 bases in length for detecting whether a *Mycobacterium avium* complex organism may be present in a sample under hybridization assay conditions, said hybridization probe having a subsequence consisting of a detection sequence selected from the group consisting of:
SEQ ID NO: 15: GGACCTTTAG ACGCATGTC,
SEQ ID NO: 16: GGACCUUUAG ACGCAUGUC,
SEQ ID NO: 17: GACATGCGTC TAAAGGTCC, and
SEQ ID NO: 18: GACAUGCGUC UAAAGGUCC;

wherein under said hybridization conditions said hybridization assay probe will hybridize to nucleic acid from said *Mycobacterium avium* complex organism to form a detectable probe:target hybrid and said hybridization assay probe will not hybridize under said hybridization conditions with nucleic acid from *Mycobacterium tuberculosis, Mycobacterium kansasii, Mycobacterium scrofulaceum, Mycobacterium simiae*, and *Mycobacterium gordonae* to form a detectable probe:non-target hybrid; and b) a helper probe consisting of a helper sequence selected from the group consisting of:
SEQ ID NO: 19: CGGGATAAGC CTGGGAAACT GGGTCTAATA CCGGATA,
SEQ ID NO: 20: TTTTGGTGGA AAGCTTTTGC GGTGTGGGAT GGGCCCGCGG,
SEQ ID NO: 21: CGGGAUAAGC CUGGGAAACU GGGUCUAAUA CCGGAUA,
SEQ ID NO: 22: TATCCGGTAT TAGACCCAGT TTCCCAGGCT TATCCCG,
SEQ ID NO: 23: UAUCCGGUAU UAGACCCAGU UUCCCAGGCU UAUCCCG,
SEQ ID NO: 24: UUUUGGUGGA AAGCUUUUGC GGUGUGGGAU GGGCCCGCGG,
SEQ ID NO: 25: CCGCGGGCCC ATCCCACACC GCAAAAGCTT TCCACCAAAA, and
SEQ ID NO: 26: CCGCGGGCCC AUCCCACACC GCAAAAGCUU UCCACCAAAA.

11. The probe mix of claim 10, wherein said hybridization assay probe consists of said detection sequence and at least one detectable label.

12. A composition for detecting a *Mycobacterium avium* complex organism comprising a nucleic acid hybrid, which is stable under high stringency hybridization assay conditions, formed between an oligonucleotide 19 to 50 bases in length having a subsequence which consists of a nucleic acid sequence selected from the group consisting of:

SEQ ID NO: 15: GGACCTTTAG ACGCATGTC,
SEQ ID NO: 16: GGACCUUUAG ACGCAUGUC,
SEQ ID NO: 17: GACATGCGTC TAAAGGTCC, and
SEQ ID NO: 18: GACAUGCGUC UAAAGGUCC, and a nucleotide polymer substantially complementary thereto, wherein under said hybridization conditions said oligonucleotide will hybridize to nucleic acid from said *Mycobacterium avium* complex organism to form a detectable oligonucleotide:target duplex and said oligonucleotide will not hybridize under said conditions with nucleic acid from *Mycobacterium tuberculosis, Mycobacterium kansasii, Mycobacterium scrofulaceum, Mycobacterium simiae*, and *Mycobacterium gordonae* to form a detectable oligonucleotide:non-target hybrid.

13. A method for detecting the presence of a *Mycobacterium avium* complex organism and distinguishing said *Mycobacterium avium* complex organism from *Mycobacterium tuberculosis, Mycobacterium kansasii, Mycobacterium scrofulaceum, Mycobacterium simiae*, and *Mycobacterium gordonae*, comprising the steps of:

a) contacting a sample under hybridization assay conditions with a nucleic acid hybridization assay probe able to hybridize under said hybridization assay conditions to a *Mycobacterium avium* complex organism target nucleic acid sequence, said hybridization assay probe comprising a nucleic acid sequence selected from the group consisting of:
SEQ ID NO: 15: GGACCTTTAG ACGCATGTC,
SEQ ID NO: 16: GGACCUUUAG ACGCAUGUC,
SEQ ID NO: 17: GACATGCGTC TAAAGGTCC, and
SEQ ID NO: 18: GACAUGCGUC UAAAGGUCC,
wherein under said hybridization conditions said hybridization assay probe will hybridize to nucleic acid from said *Mycobacterium avium* complex organism to form a detectable probe:target hybrid and said hybridization assay probe will not hybridize under said hybridization conditions with nucleic acid from *Mycobacterium tuberculosis, Mycobacterium kansasii, Mycobacterium scrofulaceum, Mycobacterium simiae*, and *Mycobacterium gordonae* to form a detectable probe:non-target hybrid; and b) detecting the presence of said hybridization assay probe hybridized to said *Mycobacterium avium* complex organism target nucleic acid sequence as an indication of the presence of said *Mycobacterium avium* complex organism.

14. A method for detecting the presence of a *Mycobacterium avium* complex organism in a sample suspected of containing a *Mycobacterium avium* complex organism other than *Mycobacterium intracellulare* and *Mycobacterium avium* comprising the steps of (a) contacting said sample suspected of containing said *Mycobacterium avium* complex organism other than *Mycobacterium intracellulare* and *Mycobacterium avium* under hybridization assay conditions with an oligonucleotide probe comprising a nucleotide base sequence consisting of a sequence selected from the group consisting of:

SEQ ID NO: 15: GGACCTTTAG ACGCATGTC,
SEQ ID NO: 16: GGACCUUUAG ACGCAUGUC,
SEQ ID NO: 17: GACATGCGTC TAAAGGTCC, and
SEQ ID NO: 18: GACAUGCGUC UAAAGGUCC, wherein under said hybridization conditions said hybridization assay probe will hybridize to nucleic acid from said *Mycobacterium avium* complex organism other than *Mycobacterium intracellulare* and *Mycobacterium avium* to form a detectable probe:target hybrid and said hybridization assay probe will not hybridize under said hybridization conditions with nucleic acid from *Mycobacterium tuberculosis, Mycobacterium kansasii, Mycobacterium scrofulaceum, Mycobacterium simiae*, and *Mycobacterium gordonae* to form a detectable probe:non-target hybrid; and (b) detecting the formation of said probe:target hybrid as an indication that said *Mycobacterium avium* complex organism other than *Mycobacterium intracellulare* and *Mycobacterium avium* may be present in said sample.

15. The method of claim 14, further comprising the presence of a helper probe in said step a), said helper probe having a helper sequence selected from the consisting of:
SEQ ID NO: 19: CGGGATAAGC CTGGGAAACT GGGTCTAATA CCGGATA,
SEQ ID NO: 20: TTTTGGTGGA AAGCTTTTGC GGTGTGGGAT GGGCCCGCGG,
SEQ ID NO: 21: CGGGAUAAGC CUGGGAAACU GGGUCUAAUA CCGGAUA,
SEQ ID NO: 22: TATCCGGTAT TAGACCCAGT TTCCCAGGCT TATCCCG,
SEQ ID NO: 23: UAUCCGGUAU UAGACCCAGU UUCCCAGGCU UAUCCCG,
SEQ ID NO: 24: UUUUGGUGGA AAGCUUUUGC GGUGUGGGAU GGGCCCGCGG,
SEQ ID NO: 25: CCGCGGGCCC ATCCCACACC GCAAAAGCTT TCCACCAAAA, and
SEQ ID NO: 26: CCGCGGGCCC AUCCCACACC GCAAAAGCUU UCCACCAAAA, wherein said helper probe is up to 50 bases in length.

16. The method of claim 15, wherein said helper probe consists of said helper sequence.

17. The probe of claim 1, wherein said probe consists of at least one detectable label said nucleic acid sequence.

18. The method of claim 5, wherein said hybridization assay probe consists of at least one detectable label said nucleic acid sequence.

19. The method of claim 5, further comprising the presence of a helper probe having a helper sequence selected from the group consisting of:
SEQ ID NO: 2: GGTATTAGAC CCAGTTTCCC AGGCTTATCC CG,
SEQ ID NO: 4: GGUAWUAGAC CCAGUUUCCC AGGCUUAUCC CG,
SEQ ID NO: 6: CGGGATAAGC CTGGGAAACT GGGTCTAATA CC,
SEQ ID NO: 8: CGGGAUAAGC CUGGGAAACU GGGUCUAAUA CC,
SEQ ID NO: 9: CACCGCAAAA GCTTTCCACC AAAAGA,
SEQ ID NO: 10: CACCGCAAAA GCUUUCCACC AAAAGA,
SEQ ID NO: 11: TCTTTTGGTG GAAAGCTTTT GCGGTG, and
SEQ ID NO: 12: UCUUUUGGUG GAAAGCUUUU GCGGUG; and wherein said hybridization assay probe is 22 to 50 bases in length and said helper probe is up to 50 bases in length.

20. The method of claim 18, wherein said helper probe consists of said helper sequence.

21. The probe of claim 9, wherein said probe consists of at least one detectable label and said nucleic acid sequence.

22. The method of claim 13, wherein said hybridization assay probe consists of at least one detectable label and said nucleic acid sequence.

23. The method of claim 13, further comprising the presence of a helper probe in said step a), said helper probe having a helper sequence selected from the group consisting of:

SEQ ID NO: 19: CGGGATAAGC CTGGGAAACT GGGTCTAATA CCGGATA,

SEQ ID NO: 20: TTTTGGTGGA AAGCTTTTGC GGTGTGGGAT GGGCCCGCGG,

SEQ ID NO: 21: CGGGAUAAGC CUGGGAAACU GGGUCUAAUA CCGGAUA,

SEQ ID NO: 22: TATCCGGTAT TAGACCCAGT TTCCCAGGCT TATCCCG,

SEQ ID NO: 23: UAUCCGGUAU UAGACCCAGU UUCCCAGGCU UAUCCCG,

SEQ ID NO: 24: UUUUGGUGGA AAGCUUUUGC GGUGUGGGAU GGGCCCGCGG,

SEQ ID NO: 25: CCGCGGGCCC ATCCCACACC GCAAAAGCTT TCCACCAAAA, and

SEQ ID NO: 26: CCGCGGGCCC AUCCCACACC GCAAAAGCUU UCCACCAAAA; and wherein said hybridization assay probe is 19 to 50 bases in length and said helper probe is up to 50 bases in length.

24. The method of claim 23, wherein said helper probe consists of said helper sequence.

25. A method for detecting the presence of a *Mycobacterium avium* complex organism and distinguishing said *Mycobacterium avium* complex organism from *Mycobacterium tuberculosis, Mycobacterium kansasii, Mycobacterium scrofulaceum, Mycobacterium simiae*, and *Mycobacterium gordonae*, comprising the steps of:

a) contacting a sample under hybridization assay conditions with a nucleic acid hybridization assay probe consisting of at least one detectable label and a nucleic acid sequence selected from the group consisting of:

SEQ ID NO: 1: CATGCGTCTA AAGGTCCTAT CC,

SEQ ID NO: 3: CAUGCGUCUA AAGGUCCUAU CC,

SEQ ID NO: 5: GGATAGGACC TTTAGACGCA TG,

SEQ ID NO: 7: GGAUAGGACC UUUAGACGCA UG,

SEQ ID NO: 15: GGACCTTTAG ACGCATGTC,

SEQ ID NO: 16: GGACCUUUAG ACGCAUGUC,

SEQ ID NO: 17: GACATGCGTC TAAAGGTCC, and

SEQ ID NO: 18: GACAUGCGUC UAAAGGUCC;

wherein under said hybridization conditions said hybridization assay probe will hybridize to nucleic acid from said *Mycobacterium avium* complex organism to form a detectable probe:target hybrid and said hybridization assay probe will not hybridize under said hybridization conditions with nucleic acid from *Mycobacterium tuberculosis, Mycobacterium kansasii, Mycobacterium scrofulaceum, Mycobacterium simiae*, and *Mycobacterium gordonae* to form a detectable probe:non-target hybrid; and b) detecting the presence of said probe hybridized to said *Mycobacterium avium* complex target nucleic acid sequence as an indication of the presence of said *Mycobacterium avium* complex organism.

26. The method of claim 25, further comprising the presence of a helper probe.

27. The method of claim 25, wherein said sequence is selected from the group consisting of:

SEQ ID NO: 1: CATGCGTCTA AAGGTCCTAT CC,

SEQ ID NO: 3: CAUGCGUCUA AAGGUCCUAU CC,

SEQ ID NO: 5: GGATAGGACC TTTAGACGCA TG, and

SEQ ID NO: 7: GGAUAGGACC UUUAGACGCA UG.

28. The method of claim 25, wherein said sequence is selected from the group consisting of:

SEQ ID NO: 15: GGACCTTTAG ACGCATGTC,

SEQ ID NO: 16: GGACCUUUAG ACGCAUGUC,

SEQ ID NO: 17: GACATGCGTC TAAAGGTCC, and

SEQ ID NO: 18: GACAUGCGUC UAAAGGUCC.

29. The probe of claim 1, wherein said probe is labeled with a radioactive reporter group.

30. The probe of claim 1, wherein said probe is labeled with a non-isotopic reporter group selected from the group consisting of: a fluorescent molecule, a chemiluminescent molecule, an enzyme, a cofactor, an enzyme substrate, and a hapten.

31. The probe of claim 1, wherein said probe is labeled with an acridinium ester.

32. The probe of claim 9, wherein said probe is labeled with a radioactive reporter group.

33. The probe of claim 9, wherein said probe is labeled with a non-isotopic reporter group selected from the group consisting of: a fluorescent molecule, a chemiluminescent molecule, an enzyme, a cofactor, an enzyme substrate, and a hapten.

34. The probe of claim 9, wherein said probe is labeled with an acridinium ester.

* * * * *

UNITED STATES PATENT AND TRADEMARK OFFICE
CERTIFICATE OF CORRECTION

PATENT NO. : 6,136,529  
DATED : October 24, 2000  
INVENTOR(S) : Hammond

Page 1 of 1

It is certified that error appears in the above-identified patent and that said Letters Patent is hereby corrected as shown below:

Column 23, claim 2,  
Line 58, replace "AGGCWUAUCC CG," with -- AGGCUUAUCC CG --.

Column 25, claim 7,  
Line 64, replace "AGGCWUAUCC CG," with -- AGGCUUAUCC CG --.

Column 28, claim 15,  
Line 20, before "consisting" insert -- group --.

Column 28, claim 18,  
Line 43, after "label" insert -- and --.

Column 28, claim 19,  
Line 50, replace "GGUAWUAGAC" with -- GGUAUUAGAC --.

Column 29, claim 20,  
Line 1, replace "18" with -- 19 --.

Signed and Sealed this

Nineteenth Day of February, 2002

Attest:

Attesting Officer

JAMES E. ROGAN  
*Director of the United States Patent and Trademark Office*

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
      (A) LENGTH: 22

```
            (B) TYPE:              nucleic acid
            (C) STRANDEDNESS:      single
            (D) TOPOLOGY:          linear (ii) SEQUENCE DESCRIPTION: SEQ ID NO: 1:

CATGCGTCTA AAGGTCCTAT CC                                                22

(2) INFORMATION FOR SEQ ID NO:    2:

(i) SEQUENCE CHARACTERISTICS:
            (A) LENGTH:            32
            (B) TYPE:              nucleic acid
            (C) STRANDEDNESS:      single
            (D) TOPOLOGY:          linear (ii) SEQUENCE DESCRIPTION: SEQ ID NO: 2:

GGTATTAGAC CCAGTTTCCC AGGCTTATCC CG                                     32

(2) INFORMATION FOR SEQ ID NO:    3:

(i) SEQUENCE CHARACTERISTICS:
            (A) LENGTH:            22
            (B) TYPE:              nucleic acid
            (C) STRANDEDNESS:      single
            (D) TOPOLOGY:          linear (ii) SEQUENCE DESCRIPTION: SEQ ID NO: 3:

CAUGCGUCUA AAGGUCCUAU CC                                                22

(2) INFORMATION FOR SEQ ID NO:    4:

(i) SEQUENCE CHARACTERISTICS:
            (A) LENGTH:            32
            (B) TYPE:              nucleic acid
            (C) STRANDEDNESS:      single
            (D) TOPOLOGY:          linear (ii) SEQUENCE DESCRIPTION: SEQ ID NO: 4:

GGUAUUAGAC CCAGUUUCCC AGGCUUAUCC CG                                     32

(2) INFORMATION FOR SEQ ID NO:    5:

(i) SEQUENCE CHARACTERISTICS:
            (A) LENGTH:            22
            (B) TYPE:              nucleic acid
            (C) STRANDEDNESS:      single
            (D) TOPOLOGY:          linear (ii) SEQUENCE DESCRIPTION: SEQ ID NO: 5:

GGATAGGACC TTTAGACGCA TG                                                22

(2) INFORMATION FOR SEQ ID NO:    6:

(i) SEQUENCE CHARACTERISTICS:
            (A) LENGTH:            32
            (B) TYPE:              nucleic acid
            (C) STRANDEDNESS:      single
            (D) TOPOLOGY:          linear (ii) SEQUENCE DESCRIPTION: SEQ ID NO: 6:

CGGGATAAGC CTGGGAAACT GGGTCTAATA CC                                     32

(2) INFORMATION FOR SEQ ID NO:    7:

(i) SEQUENCE CHARACTERISTICS:
            (A) LENGTH:            22
            (B) TYPE:              nucleic acid
```

```
            (C) STRANDEDNESS:         single
            (D) TOPOLOGY:             linear (ii) SEQUENCE DESCRIPTION: SEQ ID NO: 7:

GGAUAGGACC UUUAGACGCA UG                                            22

(2) INFORMATION FOR SEQ ID NO:   8:

(i) SEQUENCE CHARACTERISTICS:
            (A) LENGTH:              32
            (B) TYPE:                nucleic acid
            (C) STRANDEDNESS:        single
            (D) TOPOLOGY:            linear (ii) SEQUENCE DESCRIPTION: SEQ ID NO: 8:

CGGGAUAAGC CUGGGAAACU GGGUCUAAUA CC                                 32

(2) INFORMATION FOR SEQ ID NO:   9:

(i) SEQUENCE CHARACTERISTICS:
            (A) LENGTH:              26
            (B) TYPE:                nucleic acid
            (C) STRANDEDNESS:        single
            (D) TOPOLOGY:            linear (ii) SEQUENCE DESCRIPTION: SEQ ID NO: 9:

CACCGCAAAA GCTTTCCACC AAAAGA                                        26

(2) INFORMATION FOR SEQ ID NO:   10:

(i) SEQUENCE CHARACTERISTICS:
            (A) LENGTH:              26
            (B) TYPE:                nucleic acid
            (C) STRANDEDNESS:        single
            (D) TOPOLOGY:            linear (ii) SEQUENCE DESCRIPTION: SEQ ID NO: 10:

CACCGCAAAA GCUUUCCACC AAAAGA                                        26

(2) INFORMATION FOR SEQ ID NO:   11:

(i) SEQUENCE CHARACTERISTICS:
            (A) LENGTH:              26
            (B) TYPE:                nucleic acid
            (C) STRANDEDNESS:        single
            (D) TOPOLOGY:            linear (ii) SEQUENCE DESCRIPTION: SEQ ID NO: 11:

TCTTTTGGTG GAAAGCTTTT GCGGTG                                        26

(2) INFORMATION FOR SEQ ID NO:   12:

(i) SEQUENCE CHARACTERISTICS:
            (A) LENGTH:              26
            (B) TYPE:                nucleic acid
            (C) STRANDEDNESS:        single
            (D) TOPOLOGY:            linear (ii) SEQUENCE DESCRIPTION: SEQ ID NO: 12:

UCUUUUGGUG GAAAGCUUUU GCGGUG                                        26

(2) INFORMATION FOR SEQ ID NO:   13:

(i) SEQUENCE CHARACTERISTICS:
            (A) LENGTH:              55
            (B) TYPE:                nucleic acid
            (C) STRANDEDNESS:        single
```

```
        (D) TOPOLOGY:              linear (ii) SEQUENCE DESCRIPTION: SEQ ID NO: 13:

GAAATTAATA CGACTCACTA TAGGGAGACC ACAGCCGTCA CCCCACCAAC AAGCT         55

(2) INFORMATION FOR SEQ ID NO:   14:

(i) SEQUENCE CHARACTERISTICS:
        (A) LENGTH:                31
        (B) TYPE:                  nucleic acid
        (C) STRANDEDNESS:          single
        (D) TOPOLOGY:              linear (ii) SEQUENCE DESCRIPTION: SEQ ID NO: 14:

GGGATAAGCC TGGGAAACTG GGTCTAATAC C                                   31

(2) INFORMATION FOR SEQ ID NO:   15:

(i) SEQUENCE CHARACTERISTICS:
        (A) LENGTH:                19
        (B) TYPE:                  nucleic acid
        (C) STRANDEDNESS:          single
        (D) TOPOLOGY:              linear (ii) SEQUENCE DESCRIPTION: SEQ ID NO: 15:

GGACCTTTAG ACGCATGTC                                                 19

(2) INFORMATION FOR SEQ ID NO:   16:

(i) SEQUENCE CHARACTERISTICS:
        (A) LENGTH:                19
        (B) TYPE:                  nucleic acid
        (C) STRANDEDNESS:          single
        (D) TOPOLOGY:              linear (ii) SEQUENCE DESCRIPTION: SEQ ID NO: 16:

GGACCUUUAG ACGCAUGUC                                                 19

(2) INFORMATION FOR SEQ ID NO:   17:

(i) SEQUENCE CHARACTERISTICS:
        (A) LENGTH:                19
        (B) TYPE:                  nucleic acid
        (C) STRANDEDNESS:          single
        (D) TOPOLOGY:              linear (ii) SEQUENCE DESCRIPTION: SEQ ID NO: 17:

GACATGCGTC TAAAGGTCC                                                 19

(2) INFORMATION FOR SEQ ID NO:   18:

(i) SEQUENCE CHARACTERISTICS:
        (A) LENGTH:                19
        (B) TYPE:                  nucleic acid
        (C) STRANDEDNESS:          single
        (D) TOPOLOGY:              linear (ii) SEQUENCE DESCRIPTION: SEQ ID NO: 18:

GACAUGCGUC UAAAGGUCC                                                 19

(2) INFORMATION FOR SEQ ID NO:   19:

(i) SEQUENCE CHARACTERISTICS:
        (A) LENGTH:                37
        (B) TYPE:                  nucleic acid
        (C) STRANDEDNESS:          single
        (D) TOPOLOGY:              linear
```

(ii) SEQUENCE DESCRIPTION: SEQ ID NO: 19:

CGGGATAAGC CTGGGAAACT GGGTCTAATA CCGGATA                37

(2) INFORMATION FOR SEQ ID NO:   20:

(i) SEQUENCE CHARACTERISTICS:
        (A) LENGTH:            40
        (B) TYPE:              nucleic acid
        (C) STRANDEDNESS:      single
        (D) TOPOLOGY:          linear (ii) SEQUENCE DESCRIPTION: SEQ ID NO: 20:

TTTTGGTGGA AAGCTTTTGC GGTGTGGGAT GGGCCCGCGG             40

(2) INFORMATION FOR SEQ ID NO:   21:

(i) SEQUENCE CHARACTERISTICS:
        (A) LENGTH:            37
        (B) TYPE:              nucleic acid
        (C) STRANDEDNESS:      single
        (D) TOPOLOGY:          linear (ii) SEQUENCE DESCRIPTION: SEQ ID NO: 21:

CGGGAUAAGC CUGGGAAACU GGGUCUAAUA CCGGAUA                37

(2) INFORMATION FOR SEQ ID NO:   22:

(i) SEQUENCE CHARACTERISTICS:
        (A) LENGTH:            37
        (B) TYPE:              nucleic acid
        (C) STRANDEDNESS:      single
        (D) TOPOLOGY:          linear (ii) SEQUENCE DESCRIPTION: SEQ ID NO: 22:

TATCCGGTAT TAGACCCAGT TTCCCAGGCT TATCCCG                37

(2) INFORMATION FOR SEQ ID NO:   23:

(i) SEQUENCE CHARACTERISTICS:
        (A) LENGTH:            37
        (B) TYPE:              nucleic acid
        (C) STRANDEDNESS:      single
        (D) TOPOLOGY:          linear (ii) SEQUENCE DESCRIPTION: SEQ ID NO: 23:

UAUCCGGUAU UAGACCCAGU UUCCCAGGCU UAUCCCG                37

(2) INFORMATION FOR SEQ ID NO:   24:

(i) SEQUENCE CHARACTERISTICS:
        (A) LENGTH:            40
        (B) TYPE:              nucleic acid
        (C) STRANDEDNESS:      single
        (D) TOPOLOGY:          linear (ii) SEQUENCE DESCRIPTION: SEQ ID NO: 24:

UUUUGGUGGA AAGCUUUUGC GGUGUGGGAU GGGCCCGCGG             40

(2) INFORMATION FOR SEQ ID NO:   25:

(i) SEQUENCE CHARACTERISTICS:
        (A) LENGTH:            40
        (B) TYPE:              nucleic acid
        (C) STRANDEDNESS:      single
        (D) TOPOLOGY:          linear -continued (ii) SEQUENCE DESCRIPTION: SEQ ID NO: 25:

CCGCGGGCCC ATCCCACACC GCAAAAGCTT TCCACCAAAA                40

(2) INFORMATION FOR SEQ ID NO:    26:

(i) SEQUENCE CHARACTERISTICS:
        (A) LENGTH:                40
        (B) TYPE:                  nucleic acid
        (C) STRANDEDNESS:          single
        (D) TOPOLOGY:              linear (ii) SEQUENCE DESCRIPTION: SEQ ID NO: 26:

CCGCGGGCCC AUCCCACACC GCAAAAGCUU UCCACCAAAA                40